(12) United States Patent
Lauryssen et al.

(10) Patent No.: US 9,532,885 B2
(45) Date of Patent: Jan. 3, 2017

(54) DYNAMICALLY EXPANDABLE CANNULAE AND SYSTEMS AND METHODS FOR PERFORMING PERCUTANEOUS SURGICAL PROCEDURES EMPLOYING SAME

(71) Applicant: Kyphon SARL, Neuchatel (CH)

(72) Inventors: Carl Lauryssen, Beverly Hills, CA (US); Gary A. Schneiderman, Sacramento, CA (US); Darrel S. Brodke, Salt Lake City, UT (US); Frank M. Phillips, Highland Park, IL (US)

(73) Assignee: KYPHON SÀRL, Neuchâtel (CH)

( * ) Notice: Subject to any disclaimer, the term of this patent is extended or adjusted under 35 U.S.C. 154(b) by 0 days.

(21) Appl. No.: 14/935,565

(22) Filed: Nov. 9, 2015

(65) Prior Publication Data
US 2016/0058578 A1    Mar. 3, 2016

Related U.S. Application Data

(63) Continuation of application No. 12/953,882, filed on Nov. 24, 2010, now Pat. No. 9,211,140.

(51) Int. Cl.
*A61B 17/70* (2006.01)
*A61F 2/46* (2006.01)
(Continued)

(52) U.S. Cl.
CPC ......... *A61F 2/4611* (2013.01); *A61B 17/3439* (2013.01); *A61B 17/3462* (2013.01);
(Continued)

(58) Field of Classification Search
CPC ..... A61B 1/018; A61B 17/7085; A61F 2/4611
(Continued)

(56) References Cited

U.S. PATENT DOCUMENTS 3,044,461 A * 7/1962 Murdock ................. A61B 1/31
600/184
3,789,852 A * 2/1974 Kim .................... A61B 17/3439
604/104
(Continued)

*Primary Examiner* — Ellen C Hammond
*Assistant Examiner* — Stuart S Bray
(74) *Attorney, Agent, or Firm* — Sorell Lenna & Schmidt LLP

(57) ABSTRACT

In one form, a system for use in percutaneous surgical procedures includes a cannula having an elongate body extending along a longitudinal axis between a proximal end and a distal end and including a working channel dynamically expandable from a first, unexpanded configuration. The system also includes a device that is positionable in and engageable with the working channel to expand the working channel from the first configuration as the device is moved through the working channel. In response to disengagement of the device with the working channel, the working channel returns to the first, unexpanded configuration. In one aspect of this form, the device includes an interbody spinal implant that is deliverable to a surgical site through the working channel of the cannula. In another form, a method for performing a percutaneous surgical procedure is provided. However, different forms and applications are envisioned.

19 Claims, 9 Drawing Sheets

(51) Int. Cl.
*A61B 17/34* (2006.01)
*A61F 2/44* (2006.01)
*A61B 1/313* (2006.01)
*A61B 17/00* (2006.01)
*A61F 2/30* (2006.01)

(52) U.S. Cl.
CPC .......... *A61F 2/4455* (2013.01); *A61B 1/3135* (2013.01); *A61B 2017/00261* (2013.01); *A61F 2002/30579* (2013.01); *A61F 2310/00017* (2013.01); *A61F 2310/00023* (2013.01); *A61F 2310/00029* (2013.01)

(58) Field of Classification Search
USPC .................. 606/86 A, 191–192; 600/104
See application file for complete search history.

(56) References Cited

U.S. PATENT DOCUMENTS

| | | | | |
|---|---|---|---|---|
| 4,899,729 A * | 2/1990 | Gill | ............... | A61M 29/02 606/198 |
| 5,025,778 A * | 6/1991 | Silverstein | ........... | A61B 1/0008 600/104 |
| 5,259,366 A * | 11/1993 | Reydel | ............... | A61B 1/00135 383/203 |
| 5,318,588 A * | 6/1994 | Horzewski | ........ | A61M 25/0023 604/104 |
| 5,762,604 A * | 6/1998 | Kieturakis | ....... | A61B 17/00008 600/104 |
| 5,792,044 A * | 8/1998 | Foley | .................... | A61B 17/02 600/102 |
| 5,842,971 A * | 12/1998 | Yoon | .................. | A61B 17/3417 600/101 |
| 6,174,334 B1 * | 1/2001 | Suddaby | ............... | A61F 2/4455 623/17.11 |
| 6,179,873 B1 * | 1/2001 | Zientek | ................. | A61F 2/4455 623/17.11 |
| 6,187,000 B1 * | 2/2001 | Davison | ............. | A61B 17/0218 604/105 |
| 6,312,433 B1 * | 11/2001 | Butts | ..................... | A61F 2/1678 606/107 |
| 6,368,351 B1 * | 4/2002 | Glenn | .................. | A61F 2/4611 606/247 |
| 6,428,556 B1 * | 8/2002 | Chin | ................. | A61B 17/00008 606/198 |
| 6,520,991 B2 * | 2/2003 | Huene | ..................... | A61F 2/446 623/17.11 |
| 6,607,547 B1 | 8/2003 | Chin | | |
| 6,613,038 B2 * | 9/2003 | Bonutti | ............. | A61B 17/0401 600/208 |
| 6,616,600 B2 * | 9/2003 | Pauker | ............... | A61B 1/00071 600/128 |
| 6,706,052 B1 * | 3/2004 | Chin | ................. | A61B 17/00008 606/198 |
| 7,063,725 B2 * | 6/2006 | Foley | .................. | A61B 17/025 623/17.16 |
| 7,182,729 B2 * | 2/2007 | Abdelgany | ............ | A61B 17/02 600/203 |
| 7,261,688 B2 * | 8/2007 | Smith | ................. | A61B 17/0293 600/190 |
| 7,569,074 B2 * | 8/2009 | Eisermann | ............... | A61F 2/447 623/17.11 |
| 7,594,888 B2 * | 9/2009 | Raymond | .......... | A61B 17/3439 600/215 |
| 8,097,018 B2 * | 1/2012 | Malandain | ........... | A61B 17/025 606/246 |
| 8,109,972 B2 * | 2/2012 | Zucherman | ........ | A61B 17/7065 606/249 |
| 8,377,037 B2 | 2/2013 | Sachdeva et al. | | |
| 8,425,549 B2 * | 4/2013 | Lenker | ............. | A61B 17/12118 606/198 |
| 8,442,645 B2 * | 5/2013 | Zelickson | ............... | A61B 18/08 606/28 |
| 8,460,181 B2 * | 6/2013 | Saadat | ............... | A61B 1/00085 396/17 |
| 8,480,704 B2 | 7/2013 | Heiges et al. | | |
| 8,496,648 B2 | 7/2013 | Rogers | | |
| 8,945,141 B2 * | 2/2015 | Cahill | ................ | A61B 17/3439 606/108 |
| 8,974,419 B2 * | 3/2015 | Silva | ................. | A61M 25/0021 604/160 |
| 2001/0011170 A1 | 8/2001 | Davison et al. | | |
| 2005/0165411 A1 * | 7/2005 | Orban, III | ........ | A61B 17/00234 606/127 |
| 2006/0217754 A1 * | 9/2006 | Boehm, Jr. | .......... | A61B 17/025 606/191 |
| 2006/0287574 A1 * | 12/2006 | Chin | ..................... | A61M 29/02 600/114 |
| 2007/0032703 A1 * | 2/2007 | Sankaran | .......... | A61B 17/3439 600/208 |
| 2007/0060939 A1 * | 3/2007 | Lancial | ............... | A61B 1/00154 606/191 |
| 2008/0119869 A1 * | 5/2008 | Teague | ................ | A61B 17/221 606/127 |
| 2008/0183038 A1 * | 7/2008 | Tilson | ..................... | A61B 1/31 600/104 |
| 2008/0195146 A1 * | 8/2008 | Wardle | ............. | A61B 17/0644 606/219 |
| 2008/0200943 A1 * | 8/2008 | Barker | ............. | A61B 17/3439 606/192 |
| 2008/0306333 A1 * | 12/2008 | Chin | ............... | A61B 17/00008 600/104 |
| 2009/0018507 A1 * | 1/2009 | Schmitz | ............. | A61B 17/3401 604/164.03 |
| 2009/0024161 A1 * | 1/2009 | Bonutti | ............. | A61B 17/0401 606/213 |
| 2009/0275799 A1 * | 11/2009 | Saadat | ................ | A61B 1/0008 600/109 |
| 2009/0299343 A1 * | 12/2009 | Rogers | .............. | A61B 1/00078 606/1 |
| 2009/0299363 A1 | 12/2009 | Saadat et al. | | |
| 2010/0004506 A1 * | 1/2010 | Saadat | ................ | A61B 1/0008 600/109 |
| 2010/0094081 A1 * | 4/2010 | Rothe | .................... | A61B 1/0008 600/104 |
| 2010/0145267 A1 * | 6/2010 | Bishop | .............. | A61B 17/7083 604/96.01 |
| 2010/0160947 A1 * | 6/2010 | Akyuz | ................ | A61B 17/0218 606/192 |
| 2010/0217088 A1 * | 8/2010 | Heiges | ............... | A61B 17/3439 600/207 |
| 2010/0262140 A1 * | 10/2010 | Watson | ................ | A61B 1/0008 606/41 |
| 2010/0274080 A1 * | 10/2010 | Donovan | ........... | A61B 17/3421 600/104 |
| 2011/0060227 A1 * | 3/2011 | Saadat | ................ | A61B 1/0008 600/476 |
| 2011/0060298 A1 * | 3/2011 | Saadat | ................ | A61B 1/0008 604/317 |
| 2011/0065985 A1 * | 3/2011 | Wehrheim | ........... | A61B 1/0008 600/106 |
| 2011/0224742 A1 * | 9/2011 | Weisel | ............. | A61B 17/0218 606/86 R |
| 2011/0237898 A1 * | 9/2011 | Stone | ............... | A61B 17/0218 600/205 |
| 2011/0306833 A1 * | 12/2011 | Saadat | ................ | A61B 1/0008 600/109 |
| 2012/0022577 A1 * | 1/2012 | Sachdeva | ........... | A61B 1/00082 606/198 |
| 2012/0071714 A1 * | 3/2012 | Jansen | .................. | A61B 1/005 600/104 |
| 2012/0130161 A1 * | 5/2012 | Lauryssen | .......... | A61B 17/3439 600/104 |
| 2012/0239049 A1 * | 9/2012 | Truckai | .............. | A61B 17/8811 606/94 |
| 2012/0265304 A1 * | 10/2012 | Mayer | ..................... | A61F 2/442 623/17.12 |
| 2013/0012942 A1 * | 1/2013 | Nelson | .............. | A61B 17/7208 606/63 |

(56) References Cited

U.S. PATENT DOCUMENTS

| | | | |
|---|---|---|---|
| 2013/0018376 A1* | 1/2013 | Yoon | A61B 17/1617 606/79 |
| 2013/0066159 A1* | 3/2013 | Pagliuca | A61B 17/0218 600/208 |
| 2013/0090680 A1 | 4/2013 | Akyuz et al. | |
| 2013/0116504 A1* | 5/2013 | Scopton | A61B 1/0008 600/104 |
| 2013/0158414 A1 | 6/2013 | Sachdeva et al. | |
| 2014/0005639 A1 | 1/2014 | Rogers | |

* cited by examiner

DYNAMICALLY EXPANDABLE CANNULAE AND SYSTEMS AND METHODS FOR PERFORMING PERCUTANEOUS SURGICAL PROCEDURES EMPLOYING SAME

CROSS-REFERENCE TO RELATED APPLICATIONS

This application is a continuation of U.S. patent application Ser. No. 12/953,882, filed Nov. 24, 2010, which is hereby incorporated by reference herein in its entirety.

BACKGROUND

The present application relates to systems and methods for performing surgery in a patient, and more particularly, but not exclusively, relates to systems and methods that employ a cannula having a dynamically expandable working channel.

Traditional surgical procedures for pathologies located within the body involve extensive and lengthy cutting, removing, and or repositioning of skin and tissue surrounding the surgical site in order for the surgeon to access the surgical site. This type of approach may cause trauma, damage, and scarring to the tissue, and also presents risks that the tissue will become infected and that a long recovery time will be required after surgery for the tissue to heal. In some cases, these invasive procedures lead to permanent scarring and pain that can be more severe than the pain leading to the surgical intervention.

Minimally invasive surgical techniques are particularly desirable in, for example, spinal and neurosurgical applications because of the need for access to locations deep within the body and the presence of vital intervening tissues. The development of percutaneous minimally invasive spinal procedures has yielded a major improvement in reducing recovery time and post-operative pain because they require minimal, if any, muscle dissection and can be performed under local anesthesia. These benefits of minimally invasive techniques have also found application in surgeries for other locations in the body where it is desirable to minimize tissue disruption and trauma. However, current techniques for minimally invasive surgery can involve prolonged tissue retraction and require numerous steps before appropriately sized access to the surgical site is provided. Amongst other things, these aspects of current techniques can lead to greater tissue morbidity and increased complexity and duration of the surgical procedure. Thus, there remains a need for further improvements in the devices, instruments, assemblies, apparatuses, systems and methods for performing minimally invasive and other surgical techniques.

SUMMARY

In one form, a system for use in percutaneous surgical procedures includes a cannula having an elongate body extending along a longitudinal axis between a proximal end and a distal end and including a working channel dynamically expandable from a first, unexpanded configuration. The system also includes a device that is positionable in and engageable with the working channel to expand the working channel from the first configuration as the device is moved through the working channel. In response to disengagement of the device with the working channel, the working channel returns to the first, unexpanded configuration. In one aspect of this form, the device includes an interbody spinal implant that is deliverable to a surgical site through the working channel of the cannula.

In another embodiment, a surgical system includes a cannula including an elongate body extending between a proximal end and a distal end. The elongate body also includes a hollow working channel dynamically expandable from a first, unexpanded configuration. In the first configuration, the working channel is substantially uniformly sized and shaped from the proximal end to the distal end of the elongate body. The system also includes a device including at least one portion sized and configured to be inserted in and engage with the working channel to expand the working channel from the first configuration. The working channel expands from the first configuration upon engagement of the at least one portion of the device with the working channel and returns to the first configuration upon disengagement of the at least one portion of the device with the working channel. In one aspect of this embodiment, the cannula includes a pair of laterally displaceable elongate members cooperating to define the working channel and a sheath member extending around the pair of elongate members.

In yet another embodiment, a method includes providing a cannula including an elongate body extending between a proximal end and a distal end. The elongate body also includes a working channel dynamically expandable from a first, unexpanded configuration where the working channel is substantially uniformly sized and shaped from the proximal end to the distal end of the elongate body. The method also includes positioning the cannula with the working channel in the first configuration at a location adjacent to a surgical site; inserting a first instrument through the proximal end of the elongate body into the working channel and advancing the first instrument distally through the working channel toward the surgical site; expanding the working channel from the first configuration in response to insertion and advancement of the first instrument; and displacing at least a portion of the instrument from the working channel and returning the working channel to the first configuration in response to displacement of the portion of the first instrument. In a further aspect, the method also includes allowing the working channel to return to the first configuration by removing the first instrument from the working channel followed by expanding the working channel from the first configuration by inserting a second instrument through the proximal end of the elongate body into the working channel and advancing the second instrument distally through the working channel toward the surgical site.

In still another embodiment, a method includes providing a cannula including an elongate body extending between a proximal end and a distal end and including a working channel dynamically expandable from a first, unexpanded configuration; positioning the cannula with the working channel in the first configuration at a location adjacent to a surgical site; and expanding the working channel from the first, unexpanded configuration with an implant as the implant is inserted in and distally advanced through the working channel toward the surgical site. In one aspect of this embodiment, the implant is an interbody fusion device including a tapered leading end.

Another embodiment of the present application is a unique system for surgery in a patient. An additional embodiment of the present application is a unique cannula including a dynamically expandable working channel. Other embodiments include unique methods, systems, devices, kits, assemblies, equipment, and/or apparatus for use in connection with percutaneous surgical procedures. However, in other embodiments, different forms and applications are envisioned.

Further embodiments, forms, features, aspects, benefits, objects and advantages of the present application shall become apparent from the detailed description and figures provided herewith.

DESCRIPTION OF THE ILLUSTRATED EMBODIMENTS

Figure 1:
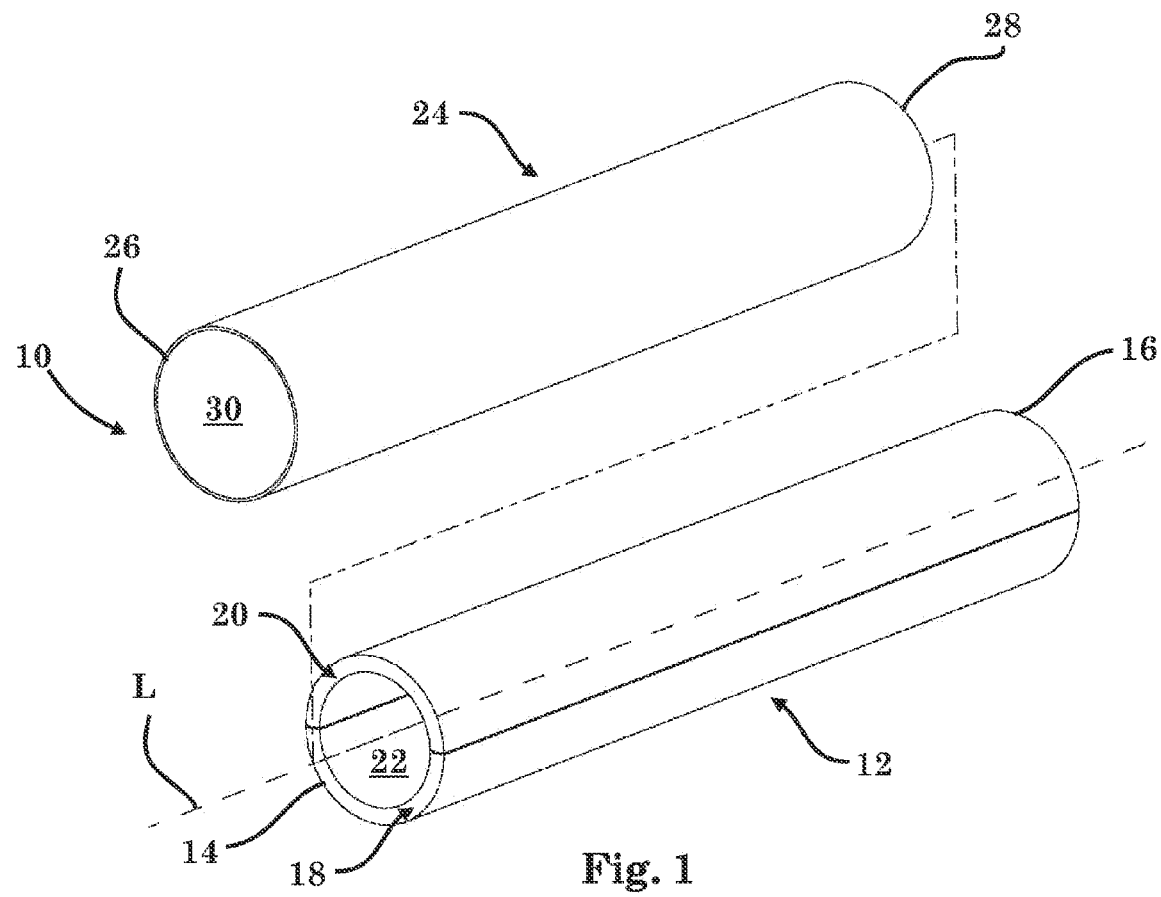
FIG. 1 is an exploded, perspective view of one embodiment of a cannula including an expandable working channel.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

Instruments, systems, apparatuses, assemblies and methods for performing surgery, including spinal surgeries that include one or more techniques such as laminotomy, laminectomy, foramenotomy, facetectomy, discectomy, interbody fusion, spinal nucleus or disc replacement, and implant insertion including interbody implants and bone engaging fasteners, for example, are provided. The surgery is performed through a dynamically expandable working channel or passageway through skin and/or tissue of the patient provided by a cannula. In one form, viewing of the surgical site at the working end of the cannula can be accomplished with naked eye visualization, microscopic viewing devices, loupes, viewing instruments mounted on the cannula, positioned over the cannula, positioned in other portals in the body, and/or through a viewing system such as lateral fluoroscopy. The cannula is movable in situ to increase the size of the working channel to facilitate access to the working space at the distal end of the cannula while minimizing trauma to tissue surrounding the cannula. The cannula can be used with any surgical approach to the spine, including anterior, posterior, posterior mid-line, lateral, postero-lateral, and/or antero-lateral approaches, and in other regions besides the spine.

In one embodiment, a system for percutaneous surgical procedures includes a cannula having an elongate body extending along a longitudinal axis between a proximal end and a distal end and including a working channel dynamically expandable from a first, unexpanded configuration. The system also includes a device that is larger than the working channel in the first configuration and is positionable in and engageable with the working channel to expand the working channel from the first configuration as the device is moved through the working channel. In response to disengagement of the device with the working channel, the working channel returns to the first, unexpanded configuration. In one aspect of this form, the device includes an interbody spinal implant that is deliverable to a surgical site through the working channel of the cannula. Still, it should be appreciated that alternative forms, aspects, configurations, arrangements and methods are contemplated with respect to the subject matter disclosed and described herein.

Figure 2:
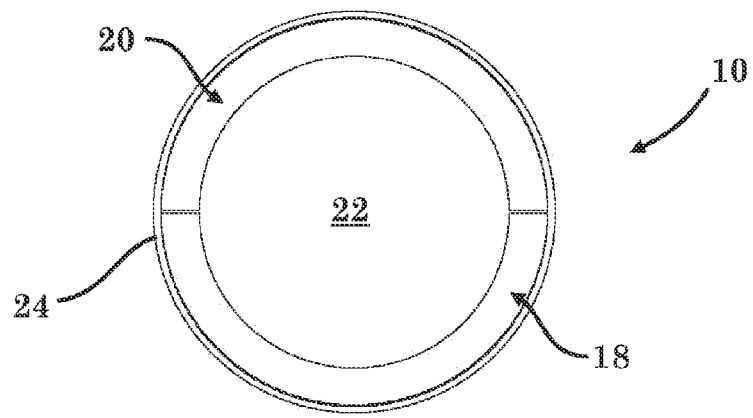
FIG. 2 is an assembled, end view of the cannula illustrated in FIG. 1.
Figure 3:
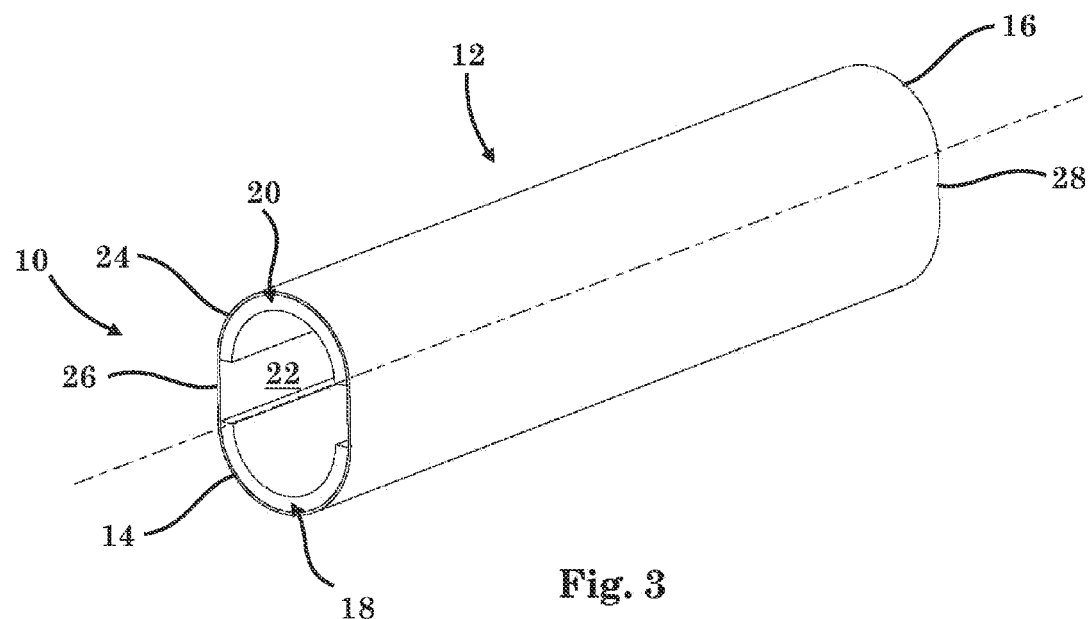
FIG. 3 is a perspective view of the cannula assembly illustrated in FIG. 1 with the working channel in an expanded configuration.

Referring now generally to FIGS. 1-4, further details regarding cannula 10 will be provided. More particularly, as illustrated in the perspective view of FIG. 1, cannula 10 includes an elongate body 12 extending along a longitudinal axis L between a proximal end 14 and a distal end 16. Elongate body 12 generally includes a length between proximal end 14 and distal end 16 that facilitates positioning of proximal end 14 above the skin of a patient when distal end 16 is positioned adjacent to the targeted surgical site. In addition, elongate body 12 includes a pair of elongate members 18, 20 that extend between proximal end 14 and distal end 16 and can include beveled ends at distal end 16 to facilitate insertion in an incision, although non-beveled ends are also contemplated. Elongate members 18, 20 have a semi-circular cross-section and cooperate to form a dynamically expandable working channel 22 having a generally circular cross-section when elongate members 18, 20 are placed adjacent one another and working channel 22 is in an unexpanded configuration as illustrated in FIGS. 1 and 2 for example. Other cross-sectional shapes are also contemplated for first and second elongate members 18, 20, such as, for example, any open sided polygonal shape including but not limited to triangular, rectangular, hexagonal or octagonal shapes, curved shapes, or combined curved/polygonal shapes. Similarly, it should be appreciated that working channel 22 can have a different cross-sectional shape dependent on the cross-sectional shape selected for elongate members 18, 20. Working channel 22 extends between and opens at proximal end 14 and distal end 16 of elongate body 12 and is generally uniformly sized and shaped from proximal end 14 to distal end 16 when it is in the unexpanded configuration shown in FIGS. 1 and 2, although forms where the size and/or shape of working channel 22 vary along its length are also possible. For example, in one non-illustrated form, it is contemplated that the size and shape of working channel 22, as well as the external profile of cannula 10, could include a smaller configuration along those portions of cannula 10 that will be positioned within the skin and tissue of the patient relative to the portions of cannula 10 that will be positioned outside of the patient during the surgical procedure.

Elongate members 18, 20 can be provided with sufficient rigidity between proximal end 14 and distal end 16 of elongate body 12 to separate and maintain separation of tissue when tissue is retracted by moving elongate members 18, 20 away from one another. For example, elongate members 18, 20 can include a thickness which provides sufficient rigidity to resist bending or bowing under the forces exerted on it by the retracted tissue. Also, the arcuately shaped portions of elongate members 18, 20 can assist in providing a sufficient section modulus or moment of inertia in the direction of movement of elongate members 18, 20 to resist bending, bowing and/or deflection forces applied during such movement. Furthermore, it is contemplated that elongate members 18, 20 can be made from any biocompatible material, including but not limited to non-reinforced polymers, carbon-reinforced polymer composites, shape-memory alloys, titanium, titanium alloys, cobalt chrome alloys, stainless steel and others as well.

As illustrated in FIG. 1, cannula 10 also includes a sheath 24 that extends between a proximal end 26 and a distal end 28. A hollow interior 30 within which elongate body 12 is positioned, as illustrated in FIG. 2 for example, extends between and opens at proximal end 26 and distal end 28 of sheath 24. Sheath 24 can be provided with a length between proximal end 26 and distal end 28 that substantially corresponds to the length of elongate body 12 between proximal end 14 and distal end 16 such that proximal ends 14, 26 and distal ends 16, 28 are flush with each other when sheath 24 is positioned around elongate members 18, 20. However, in other forms, it is contemplated that the length of sheath 24 between proximal end 26 and distal end 28 may be less than the length of elongate body 12 between proximal end 14 and distal end 16. In one aspect of this form, sheath 24 could be aligned such that only one of its ends 26, 28 is aligned with one of ends 14, 16 of elongate body 12, although aspects where sheath 24 is positioned between and not aligned with either of ends 14, 16 are also contemplated.

Sheath 24 is generally formed of a flexible or elastic material that is stretchable from an initial configuration upon the application of sufficient force and resiliently returnable to the initial configuration upon release of the force. In one form, sheath 24 can be omni-directionally stretchable, although forms are also contemplated where the ability of sheath 24 to stretch in one or more directions is limited. While not being limited to any particular form, non-limiting examples of materials from which sheath 24 may be formed include fabrics or polymers, including elastomers such as rubber and latex or other similar non-allergenic polymers, although it should be appreciated that the use any biocompatible material exhibiting the properties discussed above in this paragraph is also contemplated. In other forms however, it is also contemplated that sheath 24 could be formed of a stretchable material that does not necessarily resiliently return to its initial, unstretched state.

In one or more non-illustrated forms, it should be appreciated that sheath 24 can be attached or affixed to one or more portions of the exterior surfaces of elongate members 18, 20, although forms where elongate members 18, 20 are not attached or affixed to sheath 24 and are freely movable within hollow interior 30 are also contemplated. In one particular form, sheath 24 could be glued or otherwise adhered to elongate members 18, 20, although other means for affixing sheath 24 to elongate members 18, 20 are also possible. Among other things, it is contemplated that affixing sheath 24 to one or more portions of elongate members 18, 20 in this manner will assist in maintaining alignment of elongate members 18, 20 with one another (as illustrated in FIGS. 1 and 2 for example) as working channel 22 is expanded from and returned to its unexpanded configuration.

In addition, while not previously discussed, cannula 10 can also be provided with a brace or other support arm adjacent proximal end 14 of elongate body 12 which can be coupled with one or more operating room support structures. Examples of operating room support structures include, without limitation, support arms, braces and other linkage members which are coupled to an operating table or bed and movable to position cannula 10 relative to a surgical site of the patient. Additionally or alternatively, medical tape or other suitable adhesive materials can be attached to cannula 10 and skin or other anatomical features of the patient near the surgical site in order to stabilize cannula 10 during the surgical procedure.

Cannula 10 including elongate body 12 and sheath 24 is insertable through an incision in skin and tissue of a patient to provide working channel 22 to a surgical site. It is contemplated that elongate body 12 can initially be inserted through skin and tissue in an unexpanded, insertion configuration for working channel 22 such as the configuration illustrated in FIGS. 1 and 2 for example. Working channel 22 can have a size in the insertion configuration that allows access to the surgical site in the patient's body to perform one or more steps of the surgical procedure. However, it may be desirable during surgery to provide greater access to the surgical site in the patient's body beyond what is provided through working channel 22 in its unexpanded insertion configuration. Similarly, after insertion into the patient, working channel 22 can be enlarged by separating elongate members 18, 20 from one another along longitudinal axis L to the configuration illustrated in FIGS. 3 and 4 for example. When elongate members 18, 20 are separated from one another, working channel 22 can have a cylindrical shape with, for example, a cross-section that is oval, elliptical, circular, curved, polygonal, or combined polygonal/curved in shape.

In one form, a device or instrument to be used or positioned at the surgical site through working channel 22 generally includes a portion having a cross-sectional dimension greater than the diameter of working channel 22 in its unexpanded configuration, although use of devices and instruments through working channel 22 that are smaller than the diameter of working channel 22 in its unexpanded configuration are also contemplated. Further details regarding a more specific device in the form of an interbody spinal implant to be positioned at the surgical site through working channel 22 will be provided below in connection with FIGS. 7-9. Other examples of devices or instruments positionable through working channel 22, whether engaging the same or not, include nerve root retractors, tissue retractors, forceps, cutters, drills, scrapers, reamers, separators, rongeurs, taps, cauterization instruments, irrigation and/or aspiration instruments, illumination instruments, inserter instruments, and the like. In one aspect of the general form currently discussed, separation of elongate members 18, 20 from one another along longitudinal axis L and expansion of working channel 22 from its unexpanded configuration is initiated upon insertion of the device into working channel 22 at proximal end 14 of elongate body 12. More particularly, the portion of the device having the cross-sectional dimension greater than the diameter of working channel 22 in its unexpanded configuration can be oriented toward elongate members 18, 20 such that elongate members 18, 20 are forced apart as the device is inserted therebetween. Similarly, it should be appreciated that the distance between elongate members 18, 20 across working channel 22 in its expanded configuration will generally correspond to the dimension across the device. Stated alternatively, the amount working channel 22 is expanded from its initial configuration will be dependent on the size of the device.

Upon initial insertion of the device into working channel 22, it is contemplated that working channel 22 may only expand adjacent to proximal end 14 of elongate body 12, although expansion of working channel 22 along its length from proximal end 14 to distal end 16 is also possible. As the device is distally advanced through working channel 22, elongate members 18, 20 are progressively separated and working channel 22 is progressively expanded along its length until the device exits working channel 22 from distal end 16 of elongate body 12. In one form, it is contemplated that working channel 22 can be uniformly sized and shaped when it is expanded by the device, although forms where working channel 22 is non-uniformly sized and shaped between proximal end 14 and distal end 16 when the device is positioned therein are also contemplated.

While not previously discussed, it should be appreciated that sheath 24 stretches as elongate members 18, 20 are displaced from one another and working channel 22 is expanded from its unexpanded configuration. Upon displacement of the device from working channel 22 at distal end 16 of elongate body 12, sheath 24 resiliently returns to its unstretched state illustrated in FIGS. 1 and 2, thereby bringing elongate members 18, 20 back together and returning working channel 22 to its initial, unexpanded configuration. Similarly, sheath 24 can be utilized to automatically return working channel 22 to its unexpanded configuration without any specific action required of the surgeon besides displacement of the device from working channel 22, thereby decreasing the length of time in which the tissue surrounding cannula 10 is further retracted and the likelihood of tissue morbidity. Moreover, it is also contemplated that in addition to or in lieu of the force applied by sheath 24, the tissue surrounding cannula 10 could force elongate members 20, 22 toward one another in order to return working channel 22 to its unexpanded configuration. Dependent on the respective lengths of the device and working channel 22, in one or more forms it is also contemplated that sheath 24 may begin forcing one or more portions of working channel 22 positioned proximally of the device toward the unexpanded configuration before the device is displaced from working channel 22. Similarly, in these forms working channel 22 may be non-uniformly sized and shaped between proximal end 14 and distal end 16 when the device is positioned therein. In other non-illustrated forms however, cannula 10 can be arranged such that the separation of elongate members 18, 20 and expansion of working channel 22 is maintained, either selectively or otherwise, after the device is displaced from working channel 22. For example, in one form a mechanism such as a locking hinge is positioned between elongate members 18, 20 and allows their displacement away from one another but prevents their return toward one another once a threshold separation distance therebetween is achieved. Still, it should be appreciated that other alternative locking mechanisms are also contemplated, including those that are selectively releasable from their locked state in order to allow the return of elongate members 18, 20 toward one another.

As indicated above, certain devices or instruments to be used or positioned at the surgical site through working channel 22 displace elongate members 18, 20 from one another and expand working channel 22 along longitudinal axis L as they are inserted and advanced therethrough. Similarly, in one or more forms, it is contemplated that once the use of the device or instrument at the surgical site is complete, the device or instrument could be removed from the surgical site by proximally withdrawing it through working channel 22. As the device or instrument is moved proximally into and through working channel 22, elongate members 18, 20 are again separated along longitudinal axis L and working channel 22 is expanded from its unexpanded configuration. Once the device or instrument is removed from working channel 22 at proximal end 14, working channel 22 returns to its unexpanded configuration. If necessary, a different device or instrument could then be inserted into and expand working channel 22 between proximal end 14 and distal end 16, as appropriate, to facilitate positioning of the different device through working channel 22 to the surgical site. In other forms, it is also contemplated that more than one device or instrument can be simultaneously positioned through working channel 22.

While not previously discussed, it should be appreciated that the devices or instruments that are positioned through working channel 22 and result in its expansion from the unexpanded configuration could be provided with leading and/or trailing ends that are tapered, convexly rounded, conically shaped or otherwise suitably configured to facilitate initial engagement with the internal surfaces of working channel 22 and separation of elongate members 18, 20. Additionally or alternatively, the internal surface of working channel 22 adjacent one or both of proximal end 14 and distal end 16 may be provided with a chamfered or correspondingly tapered section that interacts with the leading and/or trailing ends of the device or instrument to facilitate engagement with working channel 22 and separation of elongate members 18, 20.

As discussed above, in other non-illustrated forms first and second elongate members 18, 20 of cannula 10 can include non-circular cross-sectional shapes, non-limiting examples of which include triangular, rectangular, hexagonal or octagonal shapes, curved shapes, or combined curved/polygonal shapes. In one form where first and second elongate members 18, 20 are rectangular shaped for example, cannula 10 includes a first axis that extends between a first pair of opposite sides that are spaced apart by a first dimension and a second axis that extends between a second pair of opposite sides that are spaced apart by a second dimension that is less than the first dimension. In this configuration, it is contemplated that cannula 10 may be inserted through an incision in skin and tissue of a patient with the first and second axes arranged in a first orientation relative to the patient and then rotated to arrange the first and second axes in a second orientation relative to the patient in order to change the orientation of working channel 22 relative to a surgical site.

For example, in one more particular form of this configuration where cannula 10 is used in spinal surgery, it may be inserted through the skin and tissue such that the first axis extends along the direction of the spinal column axis. Since the muscle tissue adjacent the spine has a fiber orientation that extends generally in the direction of the spinal column axis, positioning cannula 10 in this arrangement may initially separate the muscle tissue along the fibers. Cannula 10 may then be rotated such that the first axis extends transversely to the direction of the spinal column in order to change the orientation of working channel 22 relative to the surgical site. Since cannula 10 initially separates the muscle tissues along the fibers, its subsequent rotation such that the first axis extends transversely to the direction of the spinal column axis can decrease the likelihood of tearing and trauma to the muscle tissue compared to initial insertion of cannula 10 with the first axis extending transversely to the direction of the spinal column axis. While not discussed above, it should be appreciated that first and second elongate members 18, 20 can be displaced and working channel 22 expanded either before or after cannula 10 is rotated. In addition, it is also contemplated that cannula 10 can be initially inserted through the skin and tissue in orientations where the first axis does not extend along the direction of the spinal column axis and then rotated as discussed above to bring the first axis toward or into alignment with the direction of the spinal column axis.

As discussed above, sheath 24 can be attached or affixed to one or more portions of first and second elongate members 18, 20 which, among other things, can assist in maintaining alignment of elongate members 18, 20 as working channel 22 is expanded from and returned to its unexpanded configuration. In addition to or in lieu of attaching or affixing sheath 24 to first and second elongate members 18, 20, cannula 10 may otherwise be arranged such that elongate members 18, 20 are brought into alignment with one another as working channel 22 is returned to its unexpanded configuration. In addition, these arrangements may also maintain alignment of elongate members 18, 20 with one another when working channel 22 is expanded from its unexpanded configuration.

Figure 4:
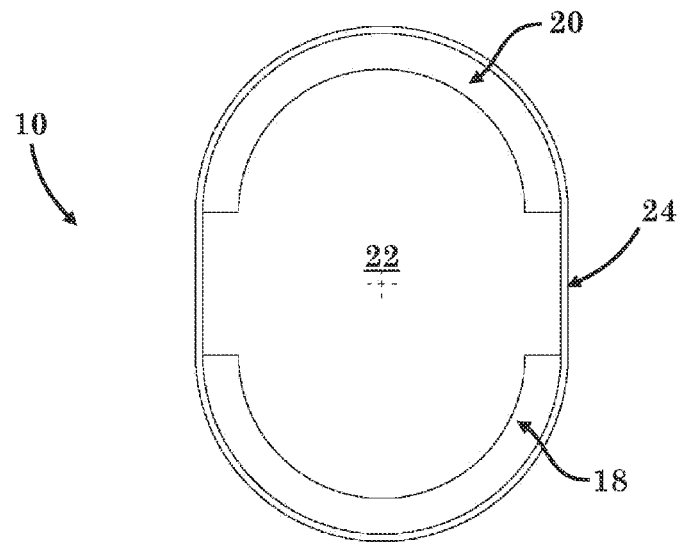
FIG. 4 is an end view of the cannula illustrated in FIG. 4.
Figure 4A:
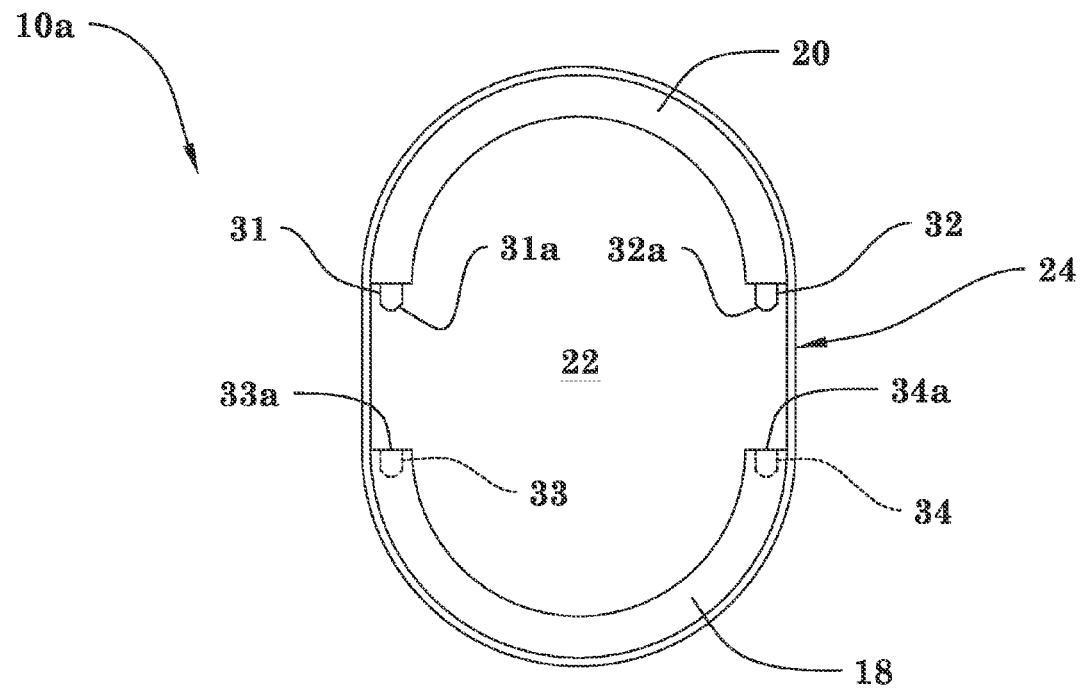
FIG. 4A is an end view of an alternative embodiment cannula assembly in an expanded configuration.
Figure 4B:
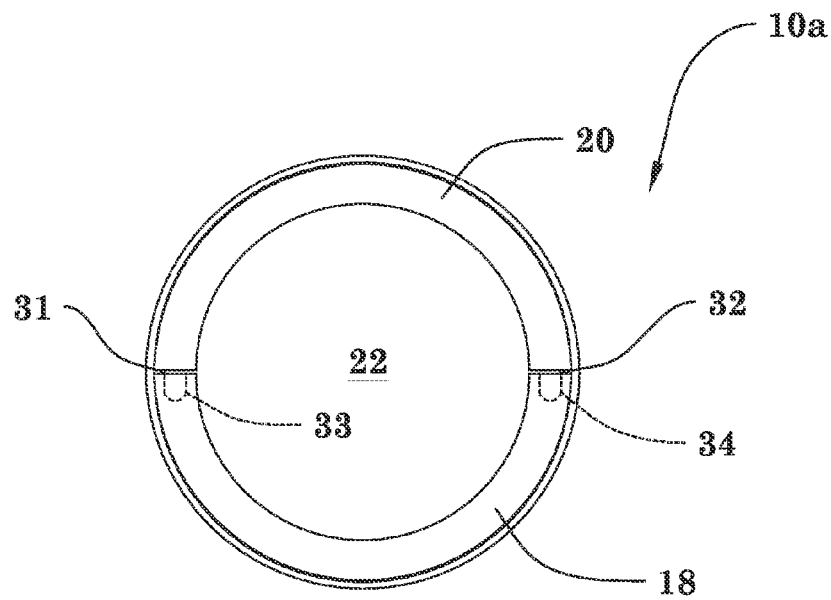
FIG. 4B is an end view of the cannula assembly illustrated in FIG. 4A in an unexpanded configuration.

With more particular reference to FIGS. 4A and 4B where like numerals refer to like features described above with respect to cannula 10, an alternative embodiment cannula 10a is configured with alignment features between elongate members 18, 20. Unless otherwise specified below, it should be appreciated that the description of the features and use of cannula 10 provided herein is also applicable to cannula 10a. In cannula 10a, elongate member 20 includes a pair of projections 31, 32 extending from its elongate, medial edges toward elongate member 18. Projections 31, 32 each terminate away from elongate member 20 at a tapered end 31a, 32a, respectively. Elongate member 18 includes a pair of receptacles 33, 34 which open through its elongate, medial edges at openings 33a, 34a, respectively. As illustrated in FIG. 4B for example, receptacles 33, 34 are configured to receive projections 31, 32 in order to maintain alignment of elongate members 18, 20 when working channel 22 is in its unexpanded configuration. Moreover, projections 31, 32 will generally maintain alignment of elongate members 18, 20 with one another as working channel 22 is expanded until tapered ends 31a, 32a are removed from receptacles 33, 34. As working channel 22 is returned to its unexpanded configuration, tapered ends 31a, 32a engage with openings 33a, 34a to guide projections 31, 32 into receptacles 33, 34 to bring and/or maintain elongate members 18, 20 in alignment with one another. While not illustrated, it should be appreciated that openings 33a, 34a can be provided with a tapered section that corresponds to the tapered configuration of tapered ends 31a, 32a to help facilitate engagement of projections 31, 32 with receptacles 33, 34. Still, other configurations for maintaining alignment of elongate members 18, 20 are also contemplated. For example, in one non-illustrated form one or both of the elongate, medial edges of one of elongate members 18, 20 can be provided with a tapered configuration that is guided into and received by a correspondingly tapered receptacle along the opposite facing elongate, medial edge of the other of elongate members 18, 20.

As suggested above, one particular application for cannulas 10, 10a is in spinal surgery. For example, with further reference to FIGS. 5-9, a method of using cannula 10 relative to a disc space D positioned between adjacent vertebral bodies $V_1$ and $V_2$ will be described, although it should be appreciated that cannula 10a could also be used in accordance with the described manner. It should also be appreciated however that while cannula 10 is described as being used in connection with a surgical procedure performed on or in relation to disc space D between adjacent vertebral bodies $V_1$ and $V_2$, use of cannulas 10, 10a at other locations along the spinal column and at other anatomical locations besides the spinal column are contemplated.

Figure 5:
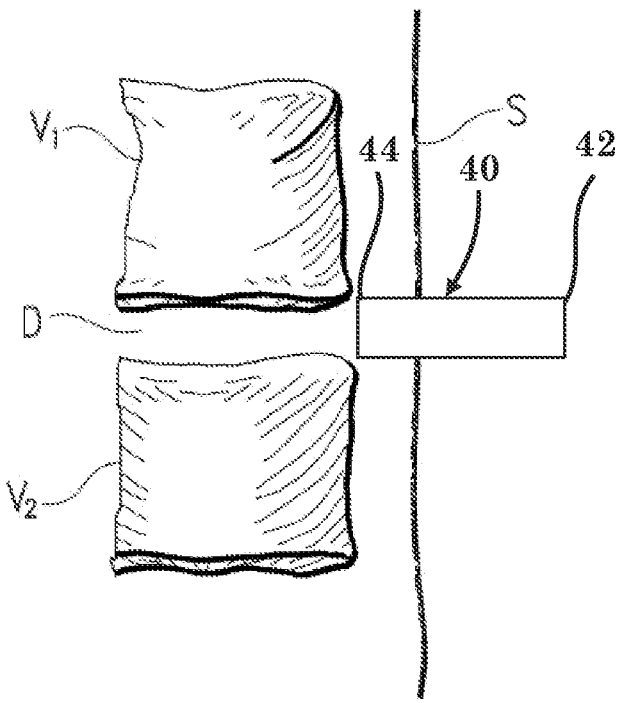
FIGS. 5-9 illustrate various steps of a minimally invasive surgical procedure employing the cannula illustrated in FIG. 1.

With reference to FIG. 5 for example, an insertion cannula 40 is inserted through an incision in the skin S and advanced to a location adjacent disc space D between adjacent vertebral bodies $V_1$ and $V_2$. Cannula 40 generally includes a working channel that extends between and opens at proximal end 42 and distal end 44. It should be appreciated that disc space D can be accessed from any of an anterior, posterior, antero-lateral, postero-lateral or lateral approach. In one form, prior to insertion of cannula 40, the skin and tissue can be sequentially dilated via a dilation instrument set (not illustrated) which can include guidewires and/or one or more tissue dilators of increasing size. The tissue dilators are inserted one over another to form a pathway through the skin and tissue to the surgical site in the patient. In such procedures, cannula 40 is positioned over an inserted dilator to form a pathway through the skin and tissue adjacent to disc space D, and the guidewires and dilators, if used, are removed from cannula 40 to leave its working channel open. However, it should be appreciated that insertion and positioning of cannula 40 without guidewires and dilators is also possible and contemplated in connection with the use of cannula 10. Furthermore, it is contemplated that cannula 10 can be positioned directly through the skin and tissue of a patient to a location adjacent a surgical site without the use of cannula 40.

Figure 6:
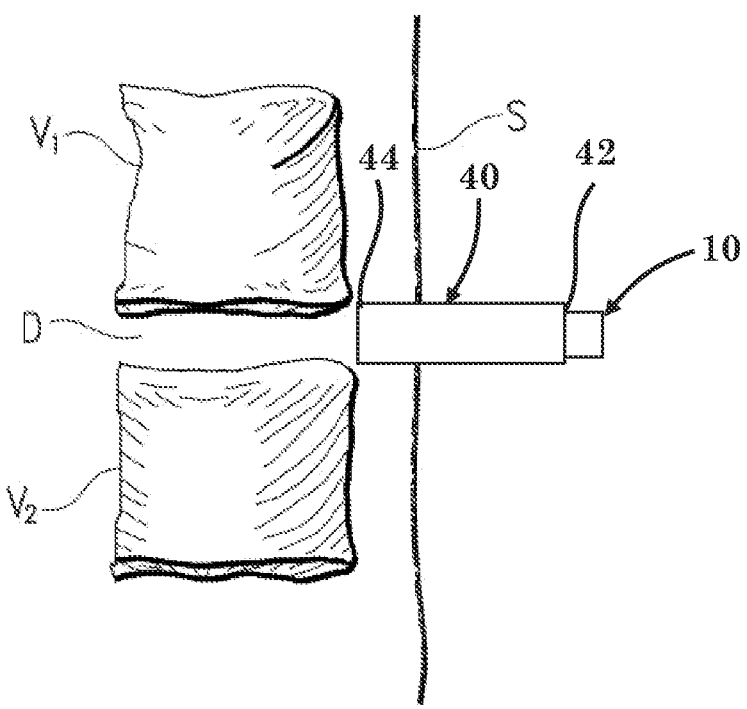
Figure 7:
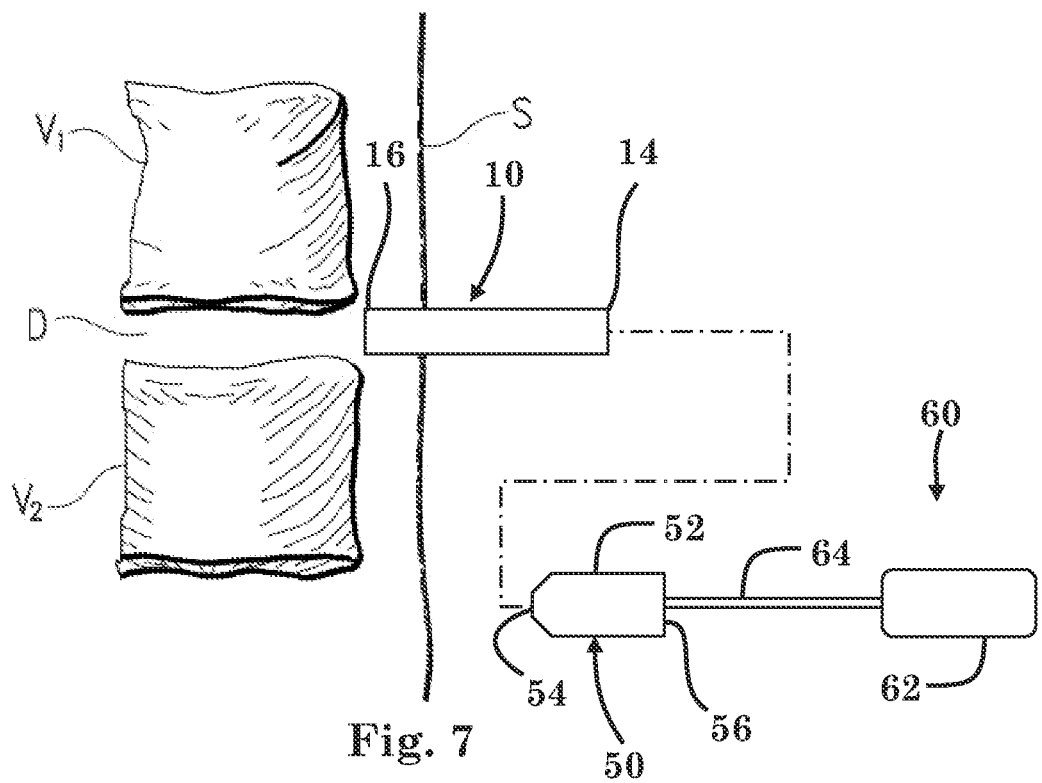

As illustrated in FIG. 6, cannula 10 is positioned in the working channel of cannula 40 after it has been properly positioned relative to the surgical site. Once positioned in the working channel of cannula 40, cannula 10 still provides access to the surgical site through working channel 22 in its unexpanded configuration. For the entire surgery or for certain procedures during the surgery, it may be necessary to increase the size of working channel 22 to facilitate passage through working channel 22 and access to the surgical site with implants, devices or instruments that are sized greater than working channel 22 in its unexpanded configuration. Similarly, in order to allow expansion of working channel 22 with the larger sized implants, devices or instruments positioned therethrough, cannula 40 is removed from the incision over cannula 10 as illustrated in FIG. 7. In one non-illustrated form, it is contemplated that a guide tube or member could be positioned in cannula 10 before cannula 40 is removed therefrom in order to provide guidance and support to cannula 10 during its removal. Once cannula 40 has been removed, cannula 10 can be coupled with one or more operating room support structures and/or attached to the patient with medical tape or another adhesive material as discussed above, although it is contemplated that cannula 10 may be directly supported by the surgeon or other medical professional during the surgical procedure if necessary.

In one form, cannula assembly 10 can be positioned relative to disc space D such that elongate members 18, 20 can be primarily or predominantly separable in the direction of the spinal column axis since the muscle tissue adjacent the spine has a fiber orientation that extends generally in the direction of the spinal column axis. The separation of elongate members 18, 20 can also separate the muscle tissue along the fibers, thus the amount of separation and the resultant tearing and trauma to the muscle tissue can be minimized. It is also contemplated in other techniques employing cannula 10 that working channel 22 can be enlarged primarily in a direction other than along the spinal column axis or in areas other than spine.

Figure 8:
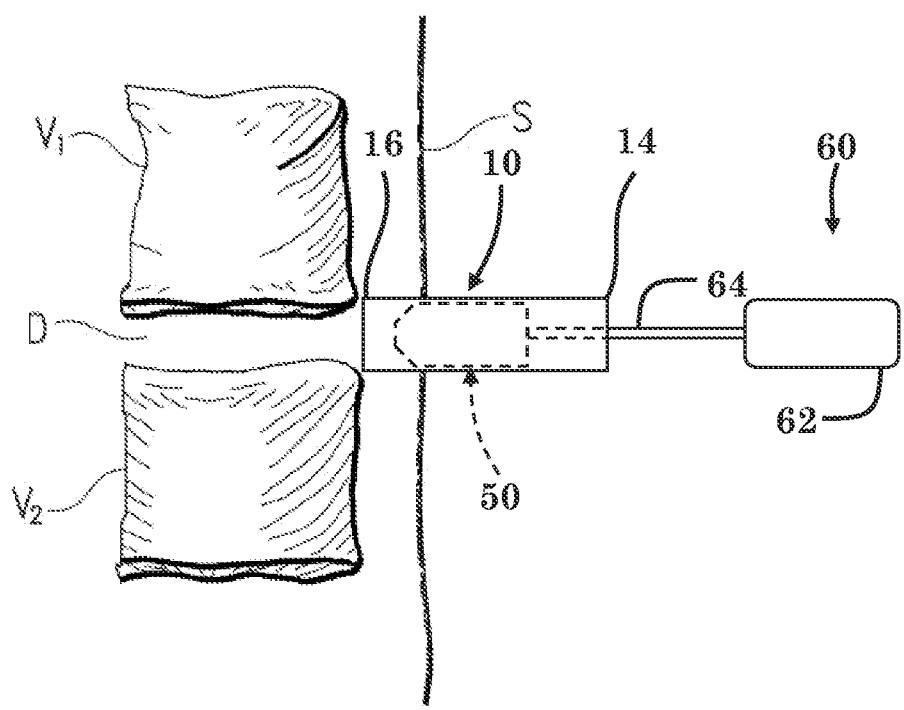
Figure 9:
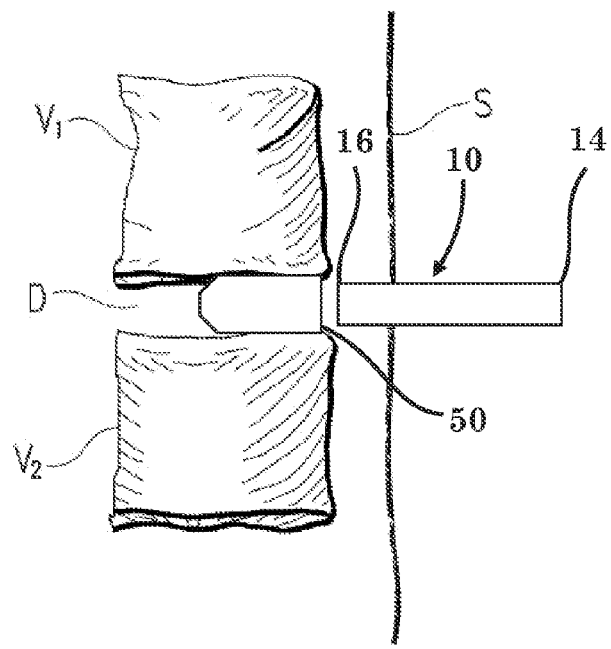

With further reference to FIGS. 7-9, an implant 50 in the form of an interbody spinal implant such as a fusion cage or spacer includes a body 52 having a leading end 54 positioned opposite of a trailing end 56 and is configured to be inserted through working channel 22 of cannula 10 to disc space D. All or part of the spinal disc material positioned between vertebral bodies $V_1$ and $V_2$ can be removed from disc space D through insertion cannula 40 and/or cannula 10 in order to create an area for implant 50 to be positioned. In addition, one or more sections of one or both of vertebral bodies $V_1$ and $V_2$ may be reamed or scraped in order to cause bleeding to facilitate or enhance fusion, if desired, between the adjacent vertebral bodies $V_1$ and $V_2$.

A driver instrument 60 includes a handle 62 positioned opposite of an elongate shaft 64 which is releasably engaged with trailing end 56 of body 52. Body 52 generally includes a height that is greater than the diameter of working channel 22 in its unexpanded configuration, such that working channel 22 must be expanded in order to facilitate positioning of implant 50 in disc space D. In one form, another larger diameter access tube or cannula can be positioned in and expand working channel 22 in order to facilitate placement of implant 50 therethrough to disc space D. Still, in another form where cannula 10 includes a locking mechanism to selectively or otherwise maintain separation of elongate members 18, 20 and expansion of working channel 22 as discussed above, a larger diameter access tube, cannula or other device can be positioned in and expand working channel 22 until the separation of elongate members 18, 20 is maintained or locked by the locking mechanism. The other access tube, cannula or device can then be removed from working channel 22, followed by positioning of implant 50 through working channel 22 in its expanded configuration to the disc space D.

However, as illustrated in FIG. 8, working channel 22 may also be expanded by direct placement and advancement of implant 50 therein. Similarly, leading end 54 includes a tapered configuration in order to facilitate engagement with the internal surface of working channel 22 and separation of elongate members 18, 20 from one another along longitudinal axis L. Moreover, tapered leading end 54 of implant 50 may also facilitate distraction of the adjacent vertebral bodies $V_1$ and $V_2$, if necessary, as implant 50 is inserted therebetween. In the illustrated form, the tapered configuration of leading end 54 generally has a linear configuration, although it should be appreciated that other tapered configurations are contemplated, including convexly rounded or conically tapered configurations, just to provide a few possibilities. A more particular example of a form in which implant 50 can be provided is disclosed in U.S. Pat. No. 7,063,725, the contents of which are incorporated herein by reference in their entirety. In another form, implant 50 is an expandable fusion device that is transitionable in situ from an unexpanded configuration to an expanded configuration. In one aspect of this form, the expandable device can include a cross-sectional configuration or dimension in its unexpanded configuration that is greater than the size of working channel 22 in its unexpanded configuration. Similarly, in its unexpanded configuration, the expandable implant can be inserted through and expand working channel 22. However, it should be appreciated that other configurations of implant 50 are also possible.

As illustrated in FIG. 8, as implant 50 is inserted in and moved distally through working channel 22 toward disc space D, elongate members 18, 20 are separated by implant 50 and working channel 22 is expanded from its unexpanded configuration. Once implant 50 is displaced from working channel 20 at distal end 16 as further shown in FIG. 9, sheath 24 brings elongate members back together and working channel 22 is returned to its unexpanded configuration. In addition, when implant 50 is in the form of the expandable fusion device as discussed above, it can be expanded to its expanded configuration once it is displaced from working channel 22 and positioned between the adjacent vertebral bodies $V_1$ and $V_2$. Moreover, in one or more forms implant 50 can be rotated relative to the vertebral bodies $V_1$ and $V_2$ after it is positioned therebetween in order to provide a desired orientation of implant 50 relative to the vertebral bodies $V_1$ and $V_2$. It should be appreciated that, if necessary, rotation of implant 50 in the form of the expandable fusion device relative to the vertebral bodies $V_1$ and $V_2$ can be performed either before or after it has been expanded. Upon final positioning of implant 50 in disc space D, driver instrument 60 can be disengaged from implant 50 and proximally withdrawn through working channel 22 in its unexpanded configuration. Once the surgical procedure has been completed, cannula assembly 10 can be removed or disengaged from the patient and/or any operating room support structures, if utilized, and then removed from its location adjacent to the surgical site with working channel 22 in its unexpanded configuration.

Figure 10:
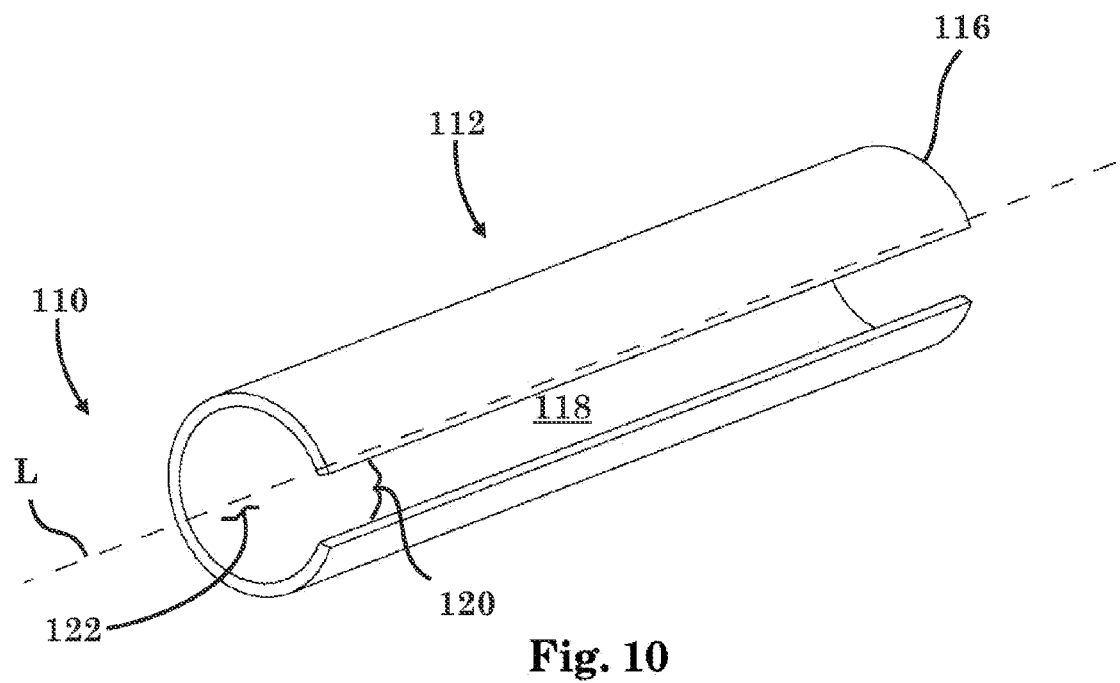
FIG. 10 is a perspective view of an alternative embodiment cannula including an expandable working channel.

An alternative embodiment cannula 110 is illustrated in a perspective view in FIG. 10. Cannula 110 includes an elongate body 112 extending along longitudinal axis L between a proximal end 114 and a distal end 116. Elongate body 112 generally includes a length between proximal end 114 and distal end 116 that facilitates positioning of proximal end 114 above the skin of a patient when distal end 116 is positioned adjacent to the targeted surgical site. Elongate body 112 includes an elongate slot 118 extending between proximal end 114 and distal end 116 such that elongate body generally has a c-shaped cross-sectional configuration, although other shapes for the cross-sectional configuration of elongate body 112 are also contemplated. Elongate slot 118 further defines an opening 120 through elongate body 112 that communicates with a dynamically expandable working channel 122 which, in the form illustrated in FIG. 10, is provided in an unexpanded configuration. In other non-illustrated forms, it is contemplated that opening 120 could be provided with a smaller or larger width than what is illustrated when working channel 122 is in the unexpanded configuration. Working channel 122 extends between and opens at proximal end 114 and distal end 116 and generally includes a circular cross-sectional configuration. In the unexpanded configuration, working channel 122 is generally uniformly sized and shaped between proximal end 114 and distal end 116. However, it is also contemplated that working channel 122 could be provided with a non-circular cross-sectional configuration and/or could be non-uniformly sized and shaped between proximal end 114 and distal end 116 in the unexpanded configuration.

Elongate body 112 is generally radially expandable about longitudinal axis L to allow expansion of working channel 122 from the unexpanded configuration as one or more objects, such as one or more devices, implants, or instruments, are engaged with and moved therethrough. Elongate body 112 is also further configured to resiliently return working channel 122 to its unexpanded configuration from displacement of the one or more objects from working channel 122. In one form, elongate body 112 may be formed of a thin metal or polymer material. However, any biocompatible material, including but not limited to non-reinforced polymers, carbon-reinforced polymer composites, shape-memory alloys, titanium, titanium alloys, cobalt chrome alloys, stainless steel and others as well, may be used to form elongate body 112, although it should be appreciated that it may be necessary to alter various design aspects of elongate body 112 depending on the material used. Additionally or alternatively, it is also contemplated that cannula 110 could be provided with a sheath similar to sheath 24 positioned around elongate body 112 to help facilitate return of working channel 122 to its unexpanded configuration. In one particular form, rather than extending entirely around elongate body 112, the sheath could be configured to only extend around a portion of elongate body 112, such as elongate slot 118 for example.

Figure 11:
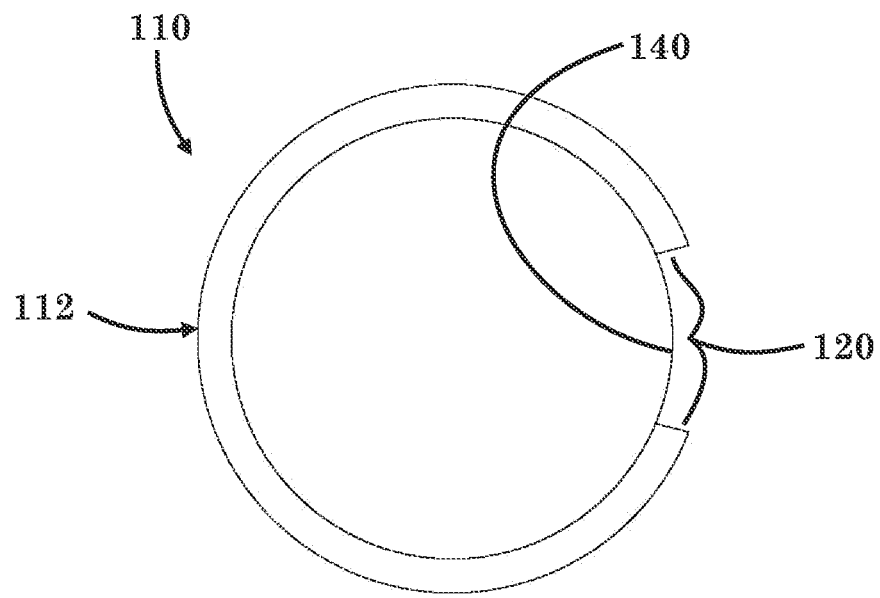
FIG. 11 is an end view of the cannula illustrated in FIG. 10 positioned relative to a delivery cannula.
Figure 12:
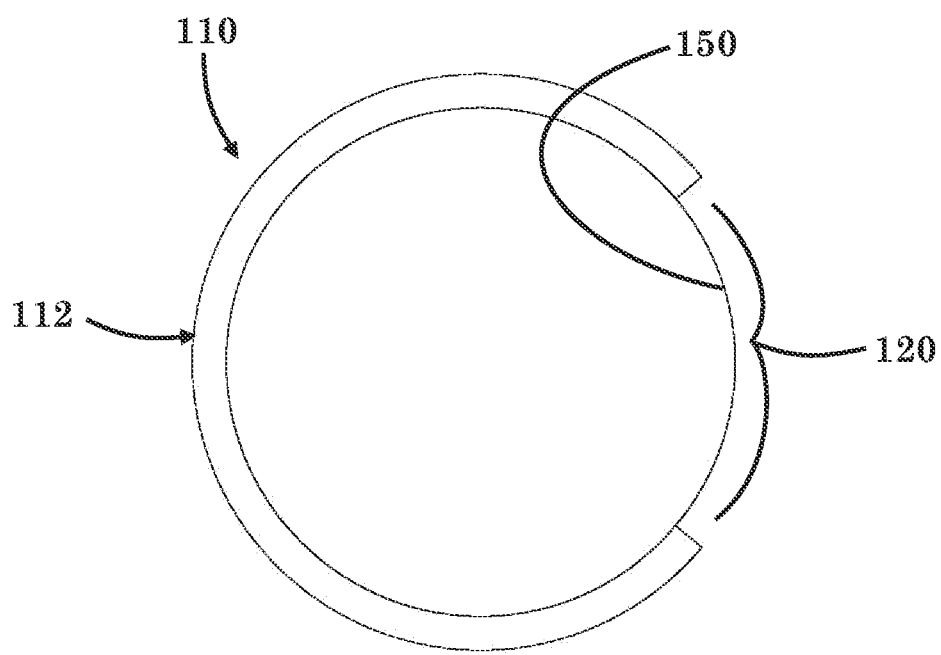
FIG. 12 is an end view of the cannula illustrated in FIG. 10 with the working channel in an expanded configuration.

As illustrated in FIG. 11, positioning cannula 110 at a surgical site with working channel 122 in the unexpanded configuration can be accomplished by positioning cannula 110 over a delivery cannula 140. Once cannula 110 has been inserted at the surgical site, delivery cannula 140 can be removed from working channel 122, which will then provide access to the surgical site in its unexpanded configuration. However, upon engagement of a larger object 150 with working channel 122 during the surgical procedure, if necessary, working channel 122 will be expanded by object 150 to allow passage of object 150 through working channel 122 to the surgical site. More particularly, as illustrated in FIG. 12, elongate body 112 generally radially expands upon insertion of object 150 such that the width of opening 120 is increased as working channel 122 is expanded. However, once object 150 is displaced from working channel 122, elongate body 112 will resiliently retract, thereby reducing the width of opening 120 and returning working channel 122 to the unexpanded configuration. Similarly, the design of cannula 110 automatically returns working channel 122 to its unexpanded configuration without any specific action required of the surgeon besides displacement of object 150 from working channel 122. As a corollary, the tissue surrounding cannula 110 is only subjected to additional retraction at those times during the surgical procedure where a larger object is positioned through working channel 122. While not previously discussed, it should be appreciated that object 150 can be any type of device, implant or surgical instrument and/or arranged as discussed above in connection with cannula 10. Moreover, in addition to or in lieu of the material properties and/or design of cannula 110, it is contemplated that the skin and/or tissue surrounding cannula 110 could influence working channel 122 back to the unexpanded configuration upon displacement of object 150 therefrom. Further, it should be appreciated that, unless otherwise specified, cannula 110 will generally have the same or substantially similar characteristics as cannula 10 and can be used in a manner similar to that described above with regard to cannula 10.

Figure 13:
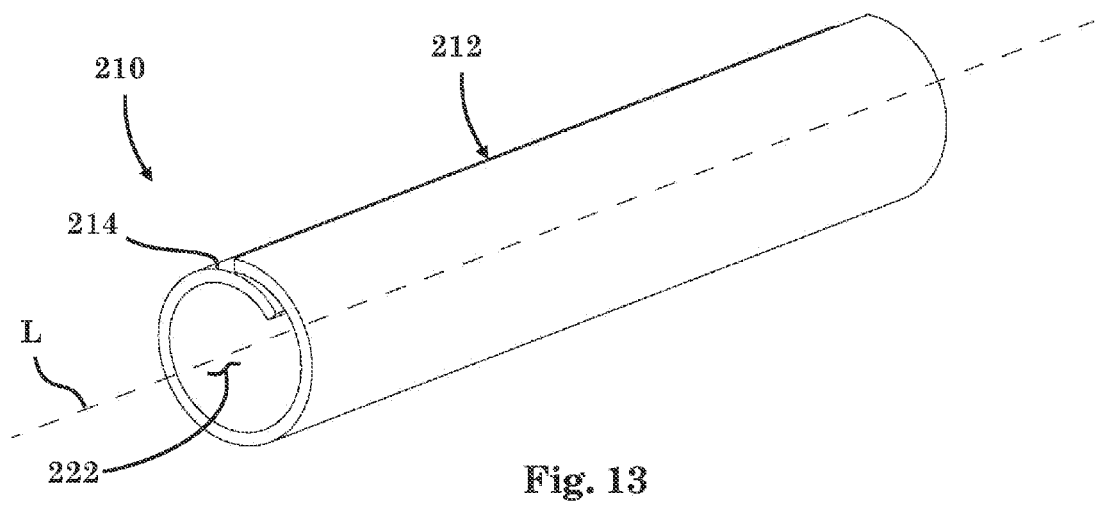
FIG. 13 is a perspective view of another alternative embodiment cannula including an expandable working channel.

Another alternative embodiment cannula 210 is illustrated in a perspective view in FIG. 13. Cannula 210 includes an elongate body 212 extending along longitudinal axis L between a proximal end 214 and a distal end 216. Elongate body 212 generally includes a length between proximal end 214 and distal end 216 that facilitates positioning of proximal end 214 above the skin of a patient when distal end 216 is positioned adjacent to the targeted surgical site. Elongate body 212 is at least partially spirally wound or coiled around longitudinal axis L from proximal end 214 to distal end 216 and includes a dynamically expandable working channel 222 which, in the form illustrated in FIG. 13, is provided in an unexpanded configuration. Working channel 222 extends between and opens at proximal end 214 and distal end 216 and, in the unexpanded configuration, is generally uniformly sized and shaped between proximal end 214 and distal end 216. However, it is also contemplated that working channel 222 could be non-uniformly sized and shaped between proximal end 214 and distal end 216 in the unexpanded configuration. In addition, it should be appreciated that the size and shape of working channel 222 in the unexpanded configuration will depend on how tightly elongate body 212 is spirally wound or coiled around longitudinal axis L. Moreover, while not previously discussed, in other non-illustrated forms elongate body 212 could be spirally wound or coiled around longitudinal axis L either more or less tightly than what is shown for the illustrated embodiment.

Elongate body 212 is generally radially expandable along longitudinal axis L as one or more objects, such as one or more devices, implants, or instruments, are engaged with and moved through working channel 222 such that elongate body 212 is uncoiled relative to longitudinal axis L and working channel 222 is expanded from the unexpanded configuration. Elongate body 212 is also further configured to resiliently return working channel 222 to its unexpanded configuration upon displacement of the one or more objects from working channel 222, although forms where elongate body 212 is configured to only partially return working channel 222 to its unexpanded configuration are also contemplated. For example, in one form, instead of working channel 222 being returned to its original unexpanded configuration where elongate body 212 is at least partially coiled or wound around longitudinal axis L, elongate body 212 could return to a c-shaped configuration similar to that described above in connection with cannula 110 such that working channel 222 will have a circular-shaped cross-sectional configuration in a partially expanded configuration. In one form, elongate body 212 may be formed of a thin metal or polymer material. However, any biocompatible material, including but not limited to non-reinforced polymers, carbon-reinforced polymer composites, shape-memory alloys, titanium, titanium alloys, cobalt chrome alloys, stainless steel and others as well, may be used to form elongate body 212, although it should be appreciated that it may be necessary to alter various design aspects of elongate body 212 depending on the material used. Additionally or alternatively, it is also contemplated that cannula 210 could be provided with a sheath similar to sheath 24 positioned around elongate body 212 to help facilitate return of working channel 222 to its unexpanded configuration.

Figure 14:
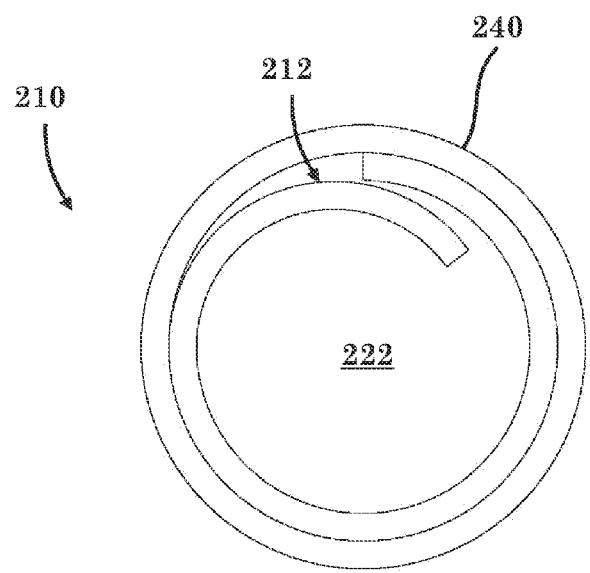
FIG. 14 is an end view of the cannula illustrated in FIG. 13 positioned relative to a delivery cannula.
Figure 15:
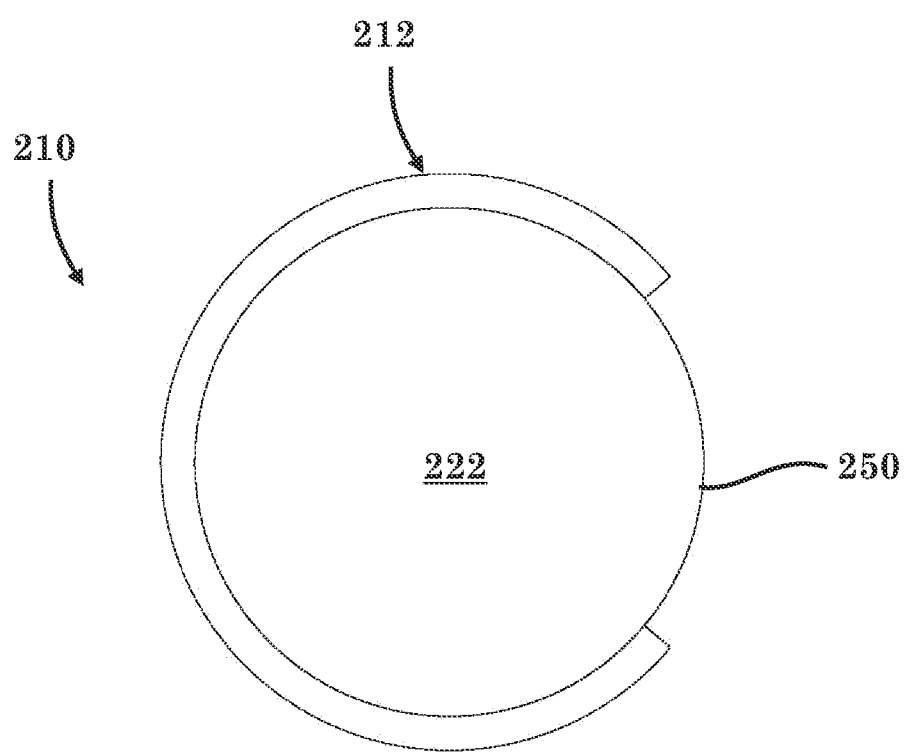
FIG. 15 is an end view of the cannula illustrated in FIG. 13 with the working channel in an expanded configuration.

As illustrated in FIG. 14, positioning cannula 210 at a surgical site with working channel 222 in the unexpanded configuration can be accomplished by positioning cannula 210 through a delivery cannula 240. Once cannula 210 has been inserted at the surgical site, delivery cannula 240 can be removed, and working channel 222 in its unexpanded configuration can provide at least some access to the surgical site. However, upon engagement of a larger object 250 with working channel 222 during the surgical procedure, if necessary, working channel 222 will be expanded by object 250 to allow passage of object 250 through working channel 222 to the surgical site. More particularly, as illustrated in FIG. 15, elongate body 212 generally radially expands upon insertion of object 250 and takes the shape of cannula 110 in its expanded configuration as discussed above in connection with FIG. 12. However, once object 250 is displaced from working channel 222, elongate body 212 will resiliently retract, thereby returning working channel 222 to the unexpanded configuration. Similarly, the design of cannula 210 automatically returns working channel 222 to its unexpanded configuration without any specific action required of the surgeon besides displacement of object 250 from working channel 222. As a corollary, the tissue surrounding cannula 210 is only subjected to additional retraction at those times during the surgical procedure where a larger object is positioned through working channel 222. While not previously discussed, it should be appreciated that object 250 can be any type of device, implant or surgical instrument and/or arranged as discussed above in connection with cannula 10. Moreover, in addition to or in lieu of the material properties and/or design of cannula 210, it is contemplated that the skin and/or tissue surrounding cannula 210 will influence working channel 222 back to the unexpanded configuration upon displacement of object 250 therefrom. Further, it should be appreciated that, unless otherwise specified, cannula 210 will generally have the same characteristics as cannula 10 and can be used in a manner similar to that described above with regard to cannula 10.

Alternative configurations and uses of the cannulae, systems and methods described herein are also contemplated. For example, in one form, one or more additional cannulae could be positioned at one or more other vertebral levels of the spinal column in order to perform a surgical procedure across multiple levels of the spinal column. In addition, the cannulae, systems and methods described herein may also be used in surgical procedures involving animals, or in demonstrations for training, education, marketing, sales and/or advertising purposes. In addition, the cannulae, systems and methods described herein may also be used on or in connection with a non-living subject such as a cadaver, training aid or model, or in connection with testing of surgical systems, surgical procedures, orthopedic devices and/or apparatus.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

What is claimed is:

1. A method, comprising:
providing a cannula extending between a proximal end and a distal end and including first and second members that define a working channel therebetween, said working channel being dynamically expandable from a first, unexpanded configuration to a second, expanded configuration, wherein in said first configuration said first member engages said second member and said working channel is substantially uniformly sized and shaped from said proximal end to said distal end and in said second configuration said first member is spaced apart from said second member;
positioning said cannula with said working channel in said first configuration at a location adjacent to a surgical site;
inserting a first instrument through said proximal end into said working channel and advancing said first instrument distally through said working channel toward said surgical site;
expanding said working channel from said first configuration to said second configuration in response to insertion and advancement of said first instrument; and
displacing at least a portion of said instrument from said working channel and returning said working channel to said first configuration in response to displacement of said portion of said first instrument.

2. The method of claim 1, wherein said cannula comprises a sheath positioned about said members.

3. The method of claim 2, wherein said sheath is affixed to one or more portions of each of said members.

4. The method of claim 2, wherein said sheath comprises an elastic material.

5. The method of claim 1, wherein said first member comprises projections that are disposed in openings in said second member when said working channel is in said first configuration.

6. The method of claim 5, wherein said projections that are spaced apart from said openings when said working channel is in said second configuration.

7. The method of claim 1, wherein said expanding is initiated upon engaging an outer surface of said first instrument with an inner surface of said working channel at said proximal end.

8. The method of claim 1, wherein said expanding includes progressively increasing a cross-sectional dimension of said working channel from said proximal end to said distal end as said first instrument is distally advanced through said working channel.

9. The method of claim 1, which includes returning at least a portion of said working channel positioned proximally of an expanding portion of said first instrument toward said first configuration as said first instrument is distally advanced through said working channel.

10. The method of claim 1, wherein displacing said portion of said first instrument includes extending said portion through said distal end to said surgical site.

11. The method of claim 1, which further includes:
allowing said working channel to return to said first configuration by removing said first instrument from said working channel; and
expanding said working channel from said first configuration by inserting a second instrument through said proximal end into said working channel and advancing said second instrument distally through said working channel toward said surgical site.

12. The method of claim 1, wherein said members each have a semi-circular cross-section such that said working channel has a generally circular cross-section when in said first configuration.

13. The method of claim 1, wherein said members are expandable opposite one another in one direction as said working channel expands from said first configuration to said second configuration.

14. A method, comprising:
providing a cannula including first and second members that define a working channel therebetween, the members being positioned within a sheath;
positioning the cannula at a location adjacent to a surgical site;
inserting an implant into the working channel and advancing the implant through the working channel toward the surgical site with an instrument such that the implant expands the working channel from a first, unexpanded configuration to a second, expanded configuration; and
positioning the implant within the surgical site such that the working channel moves from the second configuration to the first configuration, wherein the first member engages the second member when the working channel is in the first configuration and the first member is spaced apart from the second member when the working channel is in the second configuration.

15. The method of claim 14, further comprising disengaging the instrument from the implant and removing the instrument from the working channel.

16. The method of claim 14, wherein the members each have a semi-circular cross-section such that the working channel has a generally circular cross-section when in the first configuration.

17. The method of claim 14, wherein the members are expandable opposite one another in one direction as the working channel expands from the first configuration to the second configuration.

18. The method of claim 14, wherein:
the first member comprises projections that are disposed in openings in the second member when the working channel is in the first configuration; and
the projections that are disposed are spaced apart from the openings when the working channel is in the second configuration.

19. A method, comprising:
providing a cannula including first and second members that define a working channel therebetween, the members being positioned within a sheath;
positioning the cannula at a location adjacent to a surgical site;
inserting an implant into the working channel and advancing the implant through the working channel toward the surgical site with an instrument such that the implant expands the working channel from a first, unexpanded configuration to a second, expanded configuration, the members being expandable opposite one another in one direction as the working channel expands from the first configuration to the second configuration, the first member engaging the second member when the working channel is in the first configuration and the first member being spaced apart from the second member when the working channel is in the second configuration;
positioning the implant within the surgical site such that the working channel moves from the second configuration to the first configuration; and
disengaging the instrument from the implant and removing the instrument from the working channel.

* * * * *

UNITED STATES PATENT AND TRADEMARK OFFICE
CERTIFICATE OF CORRECTION

PATENT NO. : 9,532,885 B2  
APPLICATION NO. : 14/935565  
DATED : January 3, 2017  
INVENTOR(S) : Lauryssen et al.

Page 1 of 1

It is certified that error appears in the above-identified patent and that said Letters Patent is hereby corrected as shown below:

In the Specification

In Column 1, Line 10, delete "2010," and insert -- 2010, now Pat. No. 9,211,140, --, therefor.

In Column 7, Lines 40-41, delete "elongate members 20, 22" and insert -- elongate members 18, 20 --, therefor.

In Column 12, Lines 9-10, delete "working channel 20" and insert -- working channel 22 --, therefor.

In Column 14, Line 38, delete "cannula 110" and insert -- cannula 210 --, therefor.

In Column 14, Line 67, delete "cannula 110" and insert -- cannula 210 --, therefor.

Signed and Sealed this  
Fourth Day of April, 2017

Michelle K. Lee  
*Director of the United States Patent and Trademark Office*